(12) United States Patent
Stöcker (10) Patent No.: US 11,338,073 B2
(45) Date of Patent: May 24, 2022

(54) MEMBRANE FOR AN OXYGENATOR FOR GAS EXCHANGE IN THE BLOODSTREAM, OXYGENATOR HAVING SUCH A MEMBRANE, AND METHOD FOR PRODUCING SUCH A MEMBRANE

(71) Applicant: Raumedic AG, Münchberg (DE)

(72) Inventor: Martin Stöcker, Helmbrechts (DE)

(73) Assignee: RaumedicAG, Münchberg (DE)

( * ) Notice: Subject to any disclaimer, the term of this patent is extended or adjusted under 35 U.S.C. 154(b) by 754 days.

(21) Appl. No.: 15/557,964

(22) PCT Filed: Mar. 11, 2016

(86) PCT No.: PCT/EP2016/055285
§ 371 (c)(1),
(2) Date: Sep. 13, 2017

(87) PCT Pub. No.: WO2016/146524
PCT Pub. Date: Sep. 22, 2016

(65) Prior Publication Data
US 2018/0055985 A1 Mar. 1, 2018

(30) Foreign Application Priority Data
Mar. 13, 2015 (DE) .................... 10 2015 204 638.9

(51) Int. Cl.
*A61M 1/16* (2006.01)
*B01D 63/10* (2006.01)
(Continued)

(52) U.S. Cl.
CPC .......... *A61M 1/1698* (2013.01); *B01D 63/06* (2013.01); *B01D 63/08* (2013.01); *B01D 63/10* (2013.01);
(Continued)

(58) Field of Classification Search
CPC . A61M 1/1698; A61M 2207/00; B01D 63/06; B01D 63/08; B01D 63/10;
(Continued)

(56) References Cited

U.S. PATENT DOCUMENTS 3,727,612 A 4/1973 Sayers et al.
3,862,031 A * 1/1975 Leonard ................. B01D 63/14
210/321.77

(Continued)

FOREIGN PATENT DOCUMENTS

DE 10 2010 001 482 8/2011
DE 10 2013 213 318 1/2015
(Continued)

OTHER PUBLICATIONS

Machine Translation of Lauffer (EP 0 067 116 A1) (Year: 1982).*
Machine Translation of Halbach et al. (DE 102013213318 A1) (Year: 2015).*

*Primary Examiner* — Benjamin J Klein
(74) *Attorney, Agent, or Firm* — Boyle Fredrickson S.C.

(57) ABSTRACT

The invention relates to an oxygenator for gas exchange in the bloodstream, comprising a housing, a first interior chamber for blood arranged in the housing, a second interior chamber for gas arranged in the housing, and a membrane separating the interior chambers. According to the invention, the membrane has a silicone layer and a reinforcing structure reinforcing the silicone layer.

23 Claims, 3 Drawing Sheets

(51) Int. Cl.
  *B01D 63/06* (2006.01)
  *B01D 67/00* (2006.01)
  *B01D 71/70* (2006.01)
  *B01D 63/08* (2006.01)
  *B01D 69/10* (2006.01)

(52) U.S. Cl.
  CPC ......... *B01D 67/0006* (2013.01); *B01D 69/10* (2013.01); *B01D 71/70* (2013.01); *A61M 2207/00* (2013.01); *B01D 2323/30* (2013.01); *B01D 2325/04* (2013.01)

(58) Field of Classification Search
  CPC .... B01D 67/0006; B01D 69/10; B01D 71/70; B01D 2323/30; B01D 2325/04
  See application file for complete search history.

(56) References Cited

U.S. PATENT DOCUMENTS

| | | | |
|---|---|---|---|
| 3,892,533 A | | 7/1975 | Freedman et al. |
| 2009/0078644 A1 | | 3/2009 | Mues et al. |
| 2010/0132559 A1* | | 6/2010 | Ishida ................ B60R 11/0217 96/5 |

FOREIGN PATENT DOCUMENTS

| | | |
|---|---|---|
| EP | 0 067 116 | 12/1982 |
| EP | 2 109 492 | 10/2009 |
| GB | 2 086 762 | 5/1982 |

* cited by examiner

MEMBRANE FOR AN OXYGENATOR FOR GAS EXCHANGE IN THE BLOODSTREAM, OXYGENATOR HAVING SUCH A MEMBRANE, AND METHOD FOR PRODUCING SUCH A MEMBRANE

FIELD OF THE INVENTION

The invention relates to a membrane for an oxygenator for gas exchange in the blood-circulation system, to an oxygenator using this type of membrane, and also to a process for the production of this type of membrane.

BACKGROUND OF THE INVENTION

DE 10 2013 213 318 A1 discloses an asymmetrically porous membrane made of aldehyde-crosslinked thermoplastic silicone elastomer. The membrane has pores which form cavities for the exchange of substances through the membrane. To permit the production of the pores, constituents previously present in the membrane material must be removed by dissolution. Production of the membrane is complicated. For safety reasons, the membrane material is not suitable for use in an oxygenator.

EP 2 109 492 B1 discloses an oxygenator with a membrane produced from a bundle of silicone rubber tubes. Production of the membrane requires a large number of manufacturing steps. The manufacturing process imposes a certain minimum size on the oxygenator. This oxygenator is not suitable for applications involving small dimensions, in particular applications associated with transplants.

SUMMARY OF THE INVENTION

The object of the present invention is to improve a membrane for an oxygenator.

The invention achieves this object via a membrane for an oxygenator for gas exchange in the blood-circulation system. The membrane includes a silicone layer and a reinforcing structure which reinforces the silicone layer. The silicone layer is homogeneous.

The invention provides a membrane which has a silicone layer and a reinforcing structure which reinforces the silicone layer, where the silicone layer is homogeneous. Homogeneous means avoidance of large pores and/or cavities in the silicone layer. The invention is based on the discovery that pores and/or cavities are not necessary for gas exchange through the membrane. The gas exchange can take place via permeation through the solid membrane. The silicone layer, in particular the membrane, is free from cavities. There is thus no risk of leakages of plasma during the use of the membrane in an oxygenator. Another phenomenon that is prevented is the possibility of penetration of blood through a porous membrane as a consequence of pore-size variations that can occur by way of example in a production process as in DE 10 2013 213 318 A1. Transfer of blood through the membrane of the invention is reliably prevented. The silicone layer is in particular undivided. The reinforcing structure provides adequate flexural strength to the silicone layer, which in particular comprises silicone rubber (SR). The membrane, in its entirety, is stable and has advantageous handling properties. The reinforcing structure provides adequate intrinsic stiffness to the membrane. The membrane does not therefore buckle under its own weight. The membrane is a gas-exchange membrane which separates a first internal chamber and a second internal chamber of an oxygenator from one another. The gas-exchange membrane is semipermeable. The gas-exchange membrane is impermeable to liquid, in particular impermeable to blood. The gas-exchange membrane is permeable to gas, in particular ensuring permeability to oxygen and carbon dioxide. The reinforcing structure in particular extends mainly in two dimensions. A length dimension and a width dimension of the reinforcing structure are therefore greater by at least one order of magnitude than a thickness dimension. In particular, length and width of the reinforcing structure are at least 10 times the thickness, in particular at least 100 times the thickness and in particular at most 1 000 000 times the thickness.

A membrane in which the reinforcing structure takes the form of a network simplifies the provision of the reinforcing structure. The reinforcing structure itself can have been prefabricated in an uncomplicated manner. In particular, the reinforcing structure has longitudinal elements and transverse elements connected to one another. The longitudinal elements and the transverse elements are in particular arranged respectively at equal distances from one another. The reinforcing structure comprises a regular grid, in particular a rectangular grid, and in particular a square grid. The reinforcing structure is intrinsically stiff. It is in principle also conceivable to provide a reinforcing structure in a manner where reinforcing elements are present in unconsolidated form, in particular in the form of an unconsolidated, unordered assembly, in particular in the form of reinforcing fibers, where the bonding of the unconsolidated reinforcing elements to the silicone layer brings about firstly fixing of the reinforcing elements and secondly reinforcement of the silicone layer.

A membrane in which the reinforcing structure has been embedded into the silicone layer exhibits high strength. The reinforcing structure has in particular been embedded into the silicone layer on one side. The silicone layer therefore completely surrounds an underside of the reinforcing structure. An upper side of the reinforcing structure, facing away from the underside, can remain uncovered. It is also conceivable that the reinforcing structure has been completely embedded in the silicone layer.

A membrane in which the reinforcing structure comprises polyether sulfone (PES) can be used directly for medical purposes. Polyether sulfone is approved for medical applications. In principle it is also possible to use other materials which in particular have approval for medical applications, for example polyester materials. It is essential that the material of the reinforcing structure has adequate stability and/or moldability to allow use of the membrane in the oxygenator for the separation of the internal chambers. It can be necessary, if required by the shape of the oxygenator, to mold the membrane three-dimensionally. The material of the reinforcing structure is advantageously biocompatible. However, biocompatibility is not essential. In particular when the reinforcing structure has been completely embedded in the silicone layer, it is also possible to use a material that is not biocompatible. It is also in particular possible to use a braid made of metal wire for the reinforcing structure.

A membrane with increased flexural stiffness has improved stability. The increased flexural stiffness brings about reduced elasticity in the membrane sheet, in particular in the longitudinal direction and/or in the transverse direction, both of which are perpendicular to the direction of thickness of the membrane.

A membrane in which the proportion of area through which flow can take place in the reinforcing structure is at least 90% of the total area of the reinforcing structure ensures, in particular even when the mesh width of the reinforcing structure is small, that the area used is small. In particular, almost the entire area of the reinforcing structure is available as area through which flow can take place. The use of the reinforcing structure has no disadvantageous effect on suitability as gas-exchange membrane. In particular, the proportion of area through which flow can take place is at least 92% of the total area, in particular at least 95% of the total area and in particular 98% of the total area.

A membrane in which the thickness of the reinforcing structure is at most 0.4 mm, in particular at most 0.35 mm and in particular at most 0.3 mm, makes it easier to design a small oxygenator.

A thin-layer design is made possible by a membrane in which the thickness of the silicone layer varies from 0.03 mm to 0.5 mm, in particular from 0.05 mm to 0.4 mm and in particular from 0.1 mm to 0.3 mm. In particular, the thickness of the silicone layer is at most the thickness of the reinforcing structure. It is also possible that, if required by the structure of the membrane, the thickness of the silicone layer is greater than the thickness of the reinforcing structure.

The thickness of a membrane that can advantageously be used for small oxygenators, in particular for a microoxygenator, is from 0.35 mm to 0.6 mm, in particular from 0.4 mm to 0.5 mm and in particular 0.55 mm.

An oxygenator with a membrane of the invention in essence has the advantages of the membrane itself, to which reference is hereby made. The oxygenator has a first internal chamber and, separated therefrom by the membrane, a second internal chamber. The first internal chamber allows blood to flow through the device The second internal chamber allows gas to flow through the device, in particular oxygen or carbon dioxide. The first internal chamber and the second internal chamber are arranged in a housing. The oxygenator is suitable for gas exchange in the blood-circulation system, in particular in the human blood-circulation system. In particular, long periods of use are possible which can by way of example continue for at least 30 days, examples being mobile blood-circulation support systems (ECLS and ECCOR) for patients with acute heart failure or with acute heart and lung failure. Particularly because no tube material is used, the dimensions of the membrane, and therefore of the oxygenator, can be small. The oxygenator can be a microoxygenator. Because of the reduced size of the oxygenator, a relatively small quantity of blood is required to operate the oxygenator. This is advantageous. Another phenomenon prevented is the damage that can occur to the blood in large oxygenators as a consequence of a large pressure drop in the oxygenator and turbulence in the blood. Damage to the blood can by way of example result from damage to the actual blood cells; this can lead to hemolysis.

An advantageous embodiment can be provided by an oxygenator with an exterior hollow cylinder made of a first membrane and with, arranged in the exterior hollow cylinder, an interior hollow cylinder made of a second membrane. The design of the oxygenator is space-saving and compact. The hollow cylinders are in particular arranged concentrically with respect to a longitudinal axis of the housing of the oxygenator. The first internal chamber is in particular delimited by an internal side of the exterior hollow cylinder and by an external side of the interior hollow cylinder. The first internal chamber allows blood to flow through the device. The first internal chamber therefore extends in radial direction with respect to the longitudinal axis. The first internal chamber is annular. The second internal chamber is delimited by the interior hollow cylinder. The second internal chamber allows gas to flow through the device. The area which is available for flow and which is perpendicular to the longitudinal axis of the interior hollow cylinder is circular. There can in particular be a third internal chamber provided, which is delimited by an external side of the exterior hollow cylinder and by an internal side of the housing. The third internal chamber in particular allows gas to flow through the device. This additionally improves gas exchange for the blood.

An uncomplicated design can be provided by an oxygenator in which there is a first membrane and a second membrane provided, respectively arranged spirally with respect to a longitudinal axis of the housing. The first internal chamber is delimited by the first membrane and by the second membrane. The oxygenator can advantageously have a hollow-cylindrical housing.

A reliable and controlled arrangement of the membranes within the housing can be provided by an oxygenator in which the first membrane and the second membrane are retained on a core. The core serves in particular as endclosure of the first, helical internal chamber. The other end of the helical first internal chamber, opposite to the core, can be connected to an internal side of the housing. In particular, the core is arranged concentrically with respect to the longitudinal axis.

A particularly uncomplicated design is provided by an oxygenator in which the arrangement of the membrane is in a meandering pattern. In particular, precisely one membrane is required in order to separate the first internal chamber from the second internal chamber. The oxygenator can comprise a housing which has a rectangular or square shape perpendicularly to a longitudinal axis. The first internal chamber is delimited by two adjacent, in particular paralleloriented, layers of the meandering structure of the membrane. The second internal chamber is arranged adjacent to the first internal chamber. The oxygenator can advantageously comprise a plurality of first internal chambers and/or second internal chambers, which in particular are arranged in alternation adjacently to one another. The depth of the first internal chamber and/or of the second internal chamber can be prescribed via spacers. In particular, it is conceivable that spacers having different thicknesses are provided for the first internal chamber and the second internal chamber.

Another object of the present invention is to simplify the production of a membrane for an oxygenator of the invention.

This object is achieved in the invention via a process for the production of a membrane comprising the following steps: providing a silicone layer and a reinforcing structure, using a silicone dispersion to embed the reinforcing structure into the silicone layer, and crosslinking the silicone dispersion to give a homogeneous silicone layer into which the reinforcing structure has been embedded. The invention provides that a membrane for an oxygenator can be produced in that a silicone dispersion is used for embedment of a reinforcing structure, whereupon the silicone dispersion crosslinks to give a homogeneous silicone layer into which the reinforcing structure has been embedded. The silicone layer reliably retains the reinforcing structure. The reinforcing structure stabilizes the silicone layer, which thus has good handling properties. The crosslinking of the silicone dispersion is in particular temperature- and/or time-dependent. There can also be a drying step provided. The drying can take place during and/or after the crosslinking. Subsequent dissolution, where this means dissolution that has to be carried out after the crosslinking procedure, to remove substances from the silicone layer, in particular from the silicone rubber, can be omitted. It is not necessary to form cavities and/or pores in the silicone layer in order to allow the flow of material through the membrane. The membrane of the invention allows material to flow, in particular allows gas exchange, via permeation through the solid wall.

Embodiments of the invention are explained in more detail below with reference to the drawing, in which:

Figure 1:
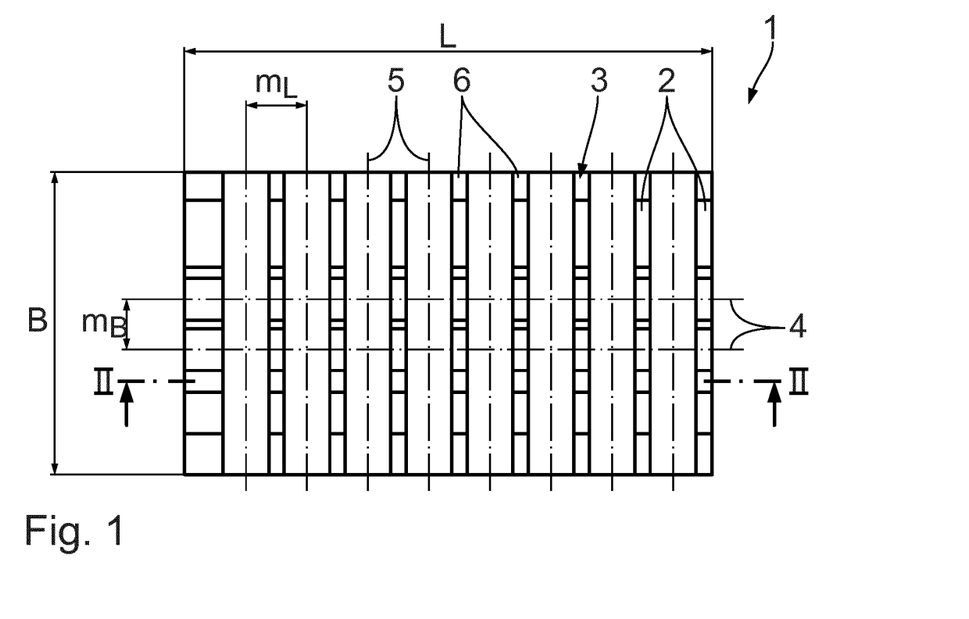
FIG. 1 is a view from one side of a membrane of the invention.
Figure 2:
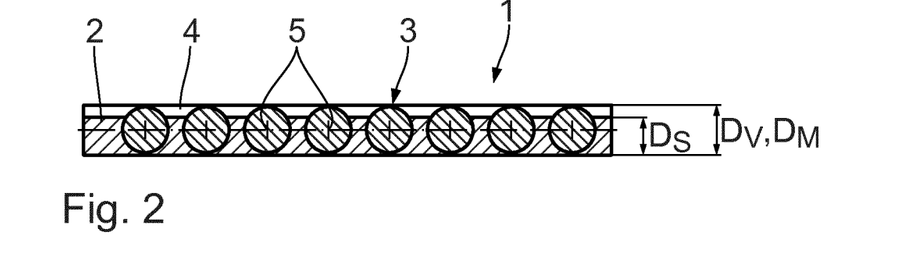
FIG. 2 is a sectional depiction corresponding to section line II-II in FIG. 1.

A membrane 1 depicted in FIG. 1 and FIG. 2 comprises a homogeneous, cavity-free silicone layer 2 and a reinforcing structure 3 which reinforces the silicone layer 2.

DESCRIPTION OF AT LEAST ONE PREFERRED EMBODIMENT

The silicone layer 2 consists in particular of silicone rubber. The silicone layer 2 provides, to the membrane 1, semipermeability needed for the use in an oxygenator. The membrane is impermeable to liquid, in particular impermeable to blood. The membrane 1 is permeable to gas, in particular permeable to oxygen ($O_2$) and/or carbon dioxide ($CO_2$). The silicone material used has good compatibility with blood.

The silicone layer 2 extends mainly in two dimensions. The expression "extends mainly in two dimensions" means that the length and width of the silicone layer 2 are markedly greater than the thickness $D_S$ of the silicone layer 2. The thickness $D_S$ in the embodiment shown is 0.2 mm. The thickness $D_S$ is advantageously from 0.1 mm to 0.3 mm. In particular, the thickness $D_S$ can be selected to be no greater than the range of thickness $D_V$ of the reinforcing structure 3.

In the embodiment shown, the reinforcing structure 3 has been embedded into the silicone layer 2 on one side. The reinforcing structure 3 has therefore been embedded into the silicone layer 2 on one side which is in particular the underside in FIG. 2. The silicone layer 2 covers the underside of the reinforcing structure 3. On an upper side opposite to the underside, the reinforcing structure 3 has at least some uncovered sections.

It is also possible that the reinforcing structure has been embedded completely in the silicone layer 2. In the case of complete embedment, the silicone layer 2 completely surrounds the reinforcing structure 3. The arrangement then has the reinforcing structure 3 protected completely within the silicone layer 2, in particular with respect to the effects of the exterior environment. Direct contact of the reinforcing structure 3 with the gas and/or the blood in the oxygenator is prevented.

In this case, i.e. in the case of complete embedment of the reinforcing structure 3, it is unimportant whether the reinforcing structure 3 has been produced from a biocompatible material. In the embodiment shown, the reinforcing structure 3 has been produced from biocompatible polyether sulfone (PES). The use of a biocompatible material for the reinforcing structure 3 is advantageous when damage occurs to the silicone layer 2 and the reinforcing structure 3 therefore comes directly into contact with the blood.

The reinforcing structure 3 takes the form of a network. The reinforcing structure 3 extends mainly in two dimensions. The reinforcing structure has longitudinal elements 4 and transverse elements 5. The longitudinal elements 4 and the transverse elements 5 have mutual interconnection. The longitudinal elements 4 and the transverse elements 5 respectively take the form of reinforcing filaments or reinforcing fibers which have been joined to one another. The reinforcing structure is intrinsically stable, i.e. has intrinsic rigidity.

In the embodiment shown, the thickness $D_V$ of the reinforcing structure is about 0.2 mm. $D_V$ is advantageously at most 0.4 mm, in particular 0.25 mm and in particular 0.3 mm.

The longitudinal elements 4 and the transverse elements 5 form a square grid with mesh width $m_L$ in longitudinal direction and mesh width $m_B$ in transverse direction. In the embodiment shown $m_L = m_B$. The mesh widths $m_L$ and $m_B$ can also be different. The mesh widths $m_L$ and $m_B$ are typically from 0.5 mm to 5 mm. It is also possible that the longitudinal elements 4 and the transverse elements 5 do not have orthogonal orientation with respect to one another.

Between the longitudinal elements 4 and the transverse elements 5 of the reinforcing structure 3, the arrangement has intervening spaces 6. The thickness $D_V$ of the reinforcing structure, i.e. the thicknesses of the longitudinal elements 4 and of the transverse elements 5, has been selected in such a way that the mesh widths $m_L$ and $m_B$ are greater than the thicknesses of the longitudinal elements 4 and of the transverse elements 5. In particular, the mesh width $m_L$ in longitudinal direction is at least five times the thickness of the transverse elements 5 and in particular at least eight times, in particular ten times. The mesh width $m_B$ in transverse direction is at least five times the thickness of the longitudinal elements 4, in particular at least eight times, and in particular at least ten times. The totality of the intervening spaces 6 forms an area available for flow through the reinforcing structure 3. The area available for flow is in particular at least 90% of the total area of the reinforcing structure 3. The total area of the reinforcing structure 3 is in particular the same as the total area of the membrane 1. The total area of the membrane 1 in the direction of flow is defined via the length L of the membrane 1 and the width B of the membrane 1. The direction of flow is the direction of thickness of the membrane 1. In the embodiment shown, where the membrane 1 is rectangular, the total area is the product of length L and width B. The depiction of the membrane 1 in FIGS. 1 and 2 is not to scale. In particular, for reasons of clarity the reinforcing structure 3, in particular the longitudinal elements 4 and the transverse elements 5, are depicted enlarged, i.e. depicted with enlarged thickness. In reality it is also possible that the reinforcing structure has reduced thickness $D_V$.

The thickness $D_M$ of the membrane 1 is from 0.35 mm to 0.6 mm. The thickness $D_M$ in the embodiment shown is about 0.45 mm.

A process for the production of the membrane 1 is explained in more detail below. The reinforcing structure 3 is first provided. In particular, the reinforcing structure 3 is placed on a non-adhering underlay. A non-adhering underlay by way of example has a surface made of polytetrafluoroethylene (PTFE). It is also possible that the entire underlay has been produced from PTFE. A silicone dispersion is used for embedment of the reinforcing structure 3. The viscosity of the silicone dispersion is 80 mPas. The aim is to form a silicone layer that is as thin as possible. A silicone dispersion with lower viscosity can form a thinner silicone layer. The viscosity of the silicone dispersion is in particular at most 200 mPas, in particular at most 100 mPas.

After the embedment procedure, the silicone dispersion crosslinks to give the silicone layer 2. The silicone dispersion crosslinks within a period of about 3 to 4 hours at a temperature of 50° C. It is possible to provide a higher crosslinking temperature. The crosslinking time is then reduced.

There can be a drying step provided, in addition to the crosslinking. The drying can take place during and/or after the crosslinking.

The process for the production of the membrane 1 is in particular environmentally friendly. Microporosity, which by way of example in the case of other membrane materials has to be generated separately, is inherently present. The additional production step for generating microporosity can be omitted.

Figure 3:
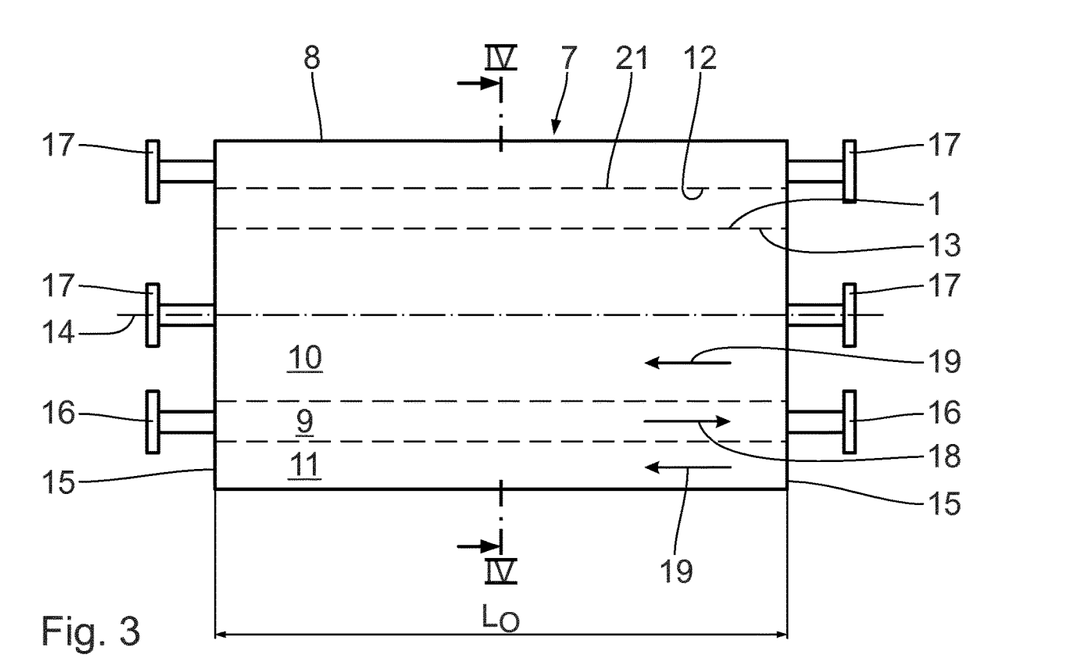
FIG. 3 is an embodiment of an oxygenator with a membrane of the invention.
Figure 4:
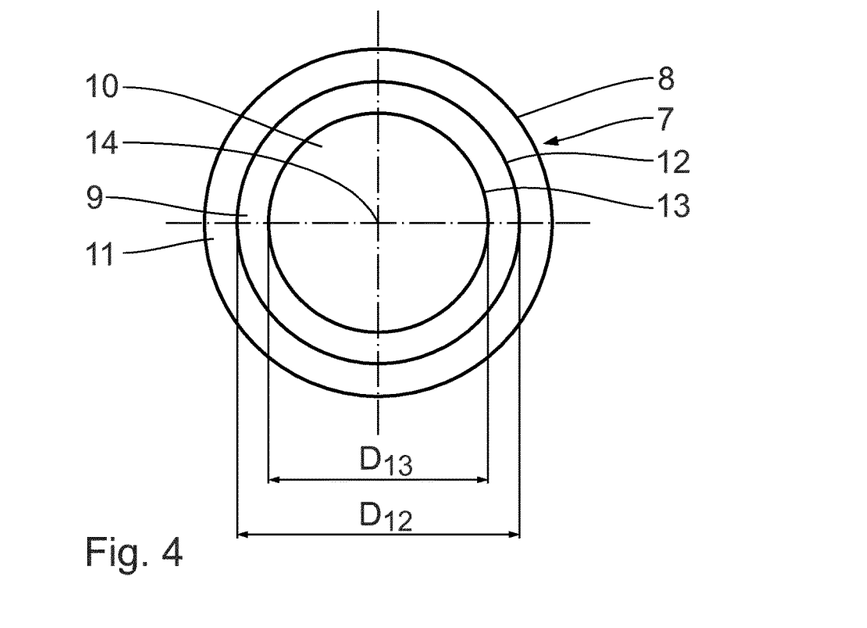
FIG. 4 is a cross-sectional depiction corresponding to the section line IV-IV in FIG. 3.

An embodiment of an oxygenator 7 shown in FIGS. 3 and 4 serves for gas exchange in the human blood-circulation system. The oxygenator 7 comprises a housing 8, a first internal chamber 9 intended for blood and arranged in the housing 8, a second internal chamber 10 intended for gas and arranged in the housing 8, and a third internal chamber 11 intended for gas and arranged in the housing 8. A first membrane separates the first internal chamber 9 from the second internal chamber 10. To this end, the first membrane, which initially has the structure in FIGS. 1 and 2 extending in two dimensions, is subjected to curvature and in particular adhesive-bonded to give an interior hollow cylinder 13. There is moreover a second membrane provided, which analogously has been subjected to curvature and adhesive-bonded to give an exterior hollow cylinder 12.

The housing 8 is hollow-cylindrical, and has a longitudinal axis 14. The arrangement has the interior hollow cylinder 13 within the exterior hollow cylinder 12. The interior hollow cylinder 13 and the exterior hollow cylinder 12 are arranged concentrically with respect to the longitudinal axis 14 in the housing 8. The first internal chamber 9 is delimited in radial direction in relation to the longitudinal axis 14 by the interior hollow cylinder 13 and the exterior hollow cylinder 12. The first internal chamber 9 is delimited in radial direction by an internal side of the exterior hollow cylinder 12 and an external side of the interior hollow cylinder 13.

The first internal chamber 9 is delimited in axial direction of the longitudinal axis 14 by an end cover 15. The first internal chamber 9 can be connected to connecting lines by way of blood ports 16. The blood ports 16 in particular have a Luer-lock connection. The arrangement has a blood port 16 on each cover 15. Blood can flow from one of the blood ports 16 through the first internal chamber, i.e. in essence along the longitudinal axis 14, to the respective other blood port 16.

The second internal chamber 10 is delimited in radial direction by the interior hollow cylinder 13. The second internal chamber 10 has a circular area oriented perpendicularly to the longitudinal axis 14. The first internal chamber 9 and the third internal chamber 11 respectively have an annular cross-sectional area perpendicularly to the longitudinal axis 14. The second internal chamber 10 is delimited by the cover 15 in axial direction. The second internal chamber 10 can be connected to connecting lines by way of gas ports 17 arranged respectively on the cover 15. The gas ports 17 have a Luer connection at which there is in particular a Luer-lock barrier. It is essential that port elements of the blood ports 16 and of the gas ports 17 are different, so that unintended connection of a blood connecting line to the gas port 17 or of a gas connecting line to the blood port 16 is reliably prevented. A difference can also be ensured in that the blood port 16 has a screw-threaded male component for connection to a corresponding female component. In this case, the gas ports 17 are not screw-threaded. Incorrect use of the oxygenator 7 is prevented.

The third internal chamber 11 is delimited in radial direction by an external side of the exterior hollow cylinder 12 and an internal side of the housing 8. The third internal chamber 11 is delimited in axial direction by the cover 15. The third internal chamber 11 can be connected to connecting lines by means of gas ports 17, which in particular are the same as the gas ports 17 of the second internal chamber 10.

The housing 8 can also have two housing halves irreleasably connected to one another, for example by adhesive bonding or embedment. Two housing halves are typically separated by a plane oriented in accordance with the section line IV-IV in FIG. 3. The orientation of a plane of separation is therefore perpendicular to the longitudinal axis 14. The oxygenator 7 ensures that there is direct contact between blood in the first internal chamber 9 and oxygen or carbon dioxide in the second and third internal chamber 10 and 11. The oxygenator 7 has a reduced size. The length $L_O$ of the oxygenator along the longitudinal axis 14 is 36 mm in the embodiment shown. The length $L_O$ of the oxygenator 7 is in particular the same as the width B of the membrane 1. The diameter $D_{13}$ of the interior hollow cylinder 13 is 21 mm in the embodiment shown. The diameter $D_{12}$ of the exterior hollow cylinder 12 is 27 mm in the embodiment shown.

The oxygenator 7 is in particular operated in that blood flows through the first internal chamber 9 along a blood flow direction 18. The blood flow direction 18 in FIG. 3 is from left to right. Oxygen and carbon dioxide flow through the second internal chamber 10 or the third internal chamber 11 along a gas flow direction 19. The gas flow direction 19 is opposite to the blood flow direction 18. The gas flow direction 19 and the blood flow direction 18 are antiparallel. The gas flow direction in FIG. 3 is from right to left.

The process for the production of the oxygenator 7 is explained in more detail below. The first membrane is first subjected to curvature and adhesive-bonded to give the exterior hollow cylinder 12. The length L of the membrane 1 here in essence forms the circumference of the exterior hollow cylinder 12. The interior hollow cylinder 13 is then formed by subjecting the second membrane to curvature and adhesive-bonding. The interior hollow cylinder 13 is arranged concentrically with respect to the exterior hollow cylinder 12. The two hollow cylinders 12 and 13 are then joined irreleasably to the housing 8. This can be achieved by way of example in that the hollow-cylindrical housing 8 is bonded, in particular adhesive-bonded, to one of the end covers 15. The hollow cylinders 12 and 13 are then introduced into the housing 8 and the ends of these are bonded to the cover 15. This bonding is achieved by either embedment or adhesive bonding. In particular, the material used for the embedment of the hollow cylinders 12 and 13 is the same as that used for the adhesive-bonding of the hollow cylinders 12 and 13. The second end cover 15 can then be placed onto the housing 8 and bonded to the housing 8 and to hollow cylinders 12 and 13.

Figure 5:
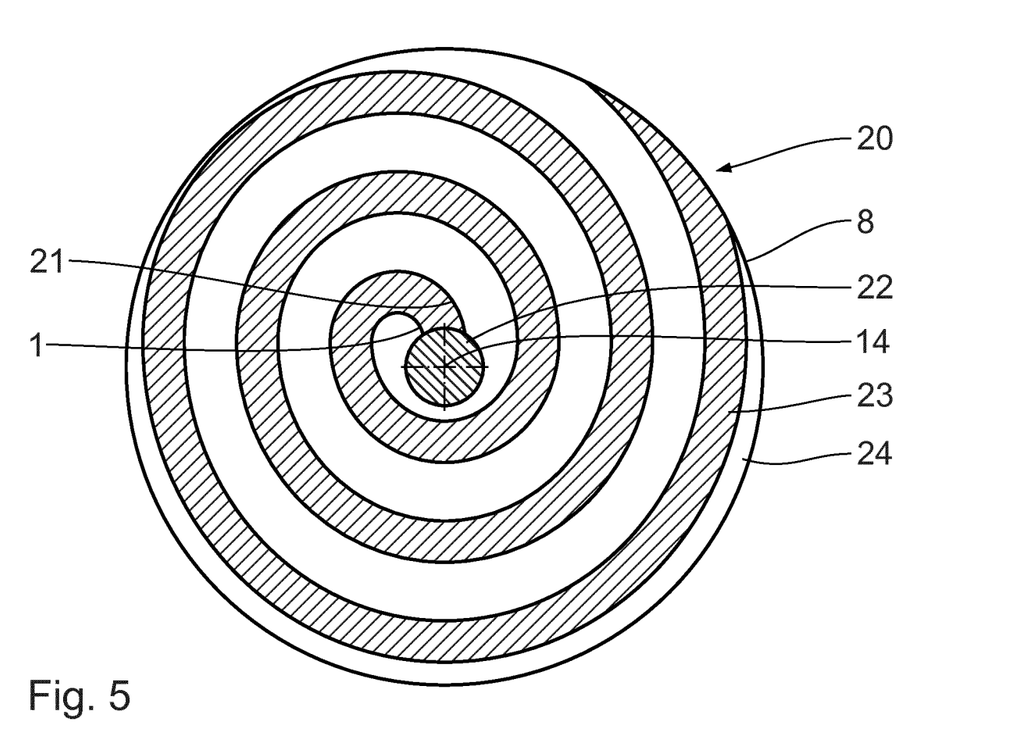
FIG. 5 is a view, corresponding to FIG. 4, of another embodiment of an oxygenator with helical membranes.

FIG. 5 shows another embodiment of an oxygenator 20. Components corresponding to those already explained above with reference to FIGS. 1 to 4 bear the same reference numbers, and detailed discussion of these is not repeated.

The essential difference of the oxygenator 20 in comparison with the previous embodiment is that the first membrane 1 and the second membrane 21 are arranged spirally with respect to the longitudinal axis 14. A first end of, respectively, the first membrane 1 and the second membrane 21 has been secured on a core 22. The core 22 is arranged concentrically with respect to the longitudinal axis 14 in the housing 8. The respective opposite ends of the membranes 1 and 21 have been secured on an internal side of the housing 8.

Because of the helical arrangement of the membranes 1 and 21, the first internal chamber 23 is helical. The second internal chamber 24 is likewise helical. There is no third internal chamber provided in the oxygenator 20. Simply for reasons of clarity, the first internal chamber 23 has been depicted with cross-hatching in the embodiment shown. It is clear that the first internal chamber 23 is hollow.

The oxygenator 20 has a blood port and a gas port on respective end covers.

Figure 6:
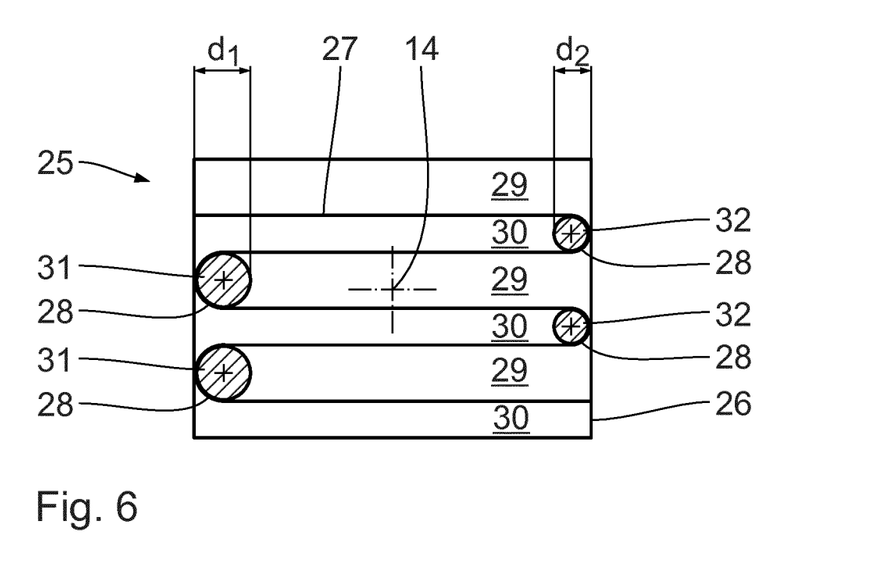
FIG. 6 is a view, corresponding to FIG. 4, of another embodiment of an oxygenator with membrane arranged in loops.

FIG. 6 shows another embodiment of an oxygenator 25. Components corresponding to those already explained above with reference to FIGS. 1 to 5 bear the same reference numbers, and detailed discussion of these is not repeated.

The essential difference in comparison with the previous embodiments is that there is precisely one membrane 1 provided. The membrane is arranged in loops in the housing 26. FIG. 6 depicts the meandering structure in the sectional plane. Layers 27 of the meandering structure are therefore oriented respectively parallel to the longitudinal axis 14 of the oxygenator 25. The layers 27 are in particular orientated parallel to one another. Two parallel, adjacent layers 27 are undivided and interconnected by way of a U-shaped deflected section 28. The deflector units 28 are in particular respectively securely connected at an external end to an internal end of the housing 26. The membrane 1 respectively separates a first internal chamber 29 from an adjacent second internal chamber 30. In the embodiment shown there are three first internal chambers 29 and three second internal chambers 30, with an alternating stacked arrangement of the internal chambers 29 and 30.

At the respective deflector units 28 there are first rollers 31 and second rollers 32 provided. The first rollers 31 are respectively arranged within the first internal chamber 29. The first rollers 31 ensure that adjacent layers 27 are arranged at a defined distance from one another. The defined distance between the adjacent layers 27 is prescribed by the diameter of the first rollers 31. The first roller 31 has a first diameter $d_1$. The first diameter $d_1$ is at most 3 mm, in particular at most 2.5 mm.

Correspondingly, the second roller 32 has a second diameter $d_2$. The second diameter $d_2$ is smaller than the first diameter $d_1$. In particular, the second diameter $d_2$ is less than 2.5 mm, in particular less than 2 mm and in particular less than 1.5 mm.

The shape of the housing 26 is rectangular. The length of the oxygenator 25 perpendicularly to the plane of the drawing of FIG. 6, i.e. along the longitudinal axis 14, is about 15 cm. The oxygenator 25 with the membrane 1 of the invention can provide improved gas exchange because of its compact and multilayered design.

What is claimed is:

1. A membrane for an oxygenator for gas exchange in a blood-circulation system, the membrane comprising: a silicone layer and a reinforcing structure which reinforces the silicone layer,
   wherein the membrane is impermeable to liquid, but permeable to gas,
   wherein the silicone layer comprises silicone rubber,
   wherein the silicone layer is free from cavities,
   wherein the reinforcing structure comprises polyether sulfone (PES), wherein the reinforcing structure comprises reinforcing elements and intervening spaces, wherein the totality of the intervening spaces forms an area available for flow through the reinforcing structure,
   wherein a proportion through said area in the reinforcing structure is at least 90% of a total area of the reinforcing structure;
   wherein a thickness of the silicone layer is smaller than a thickness of the reinforcing structure.

2. The membrane as claimed in claim 1, wherein the reinforcing structure is a network.

3. The membrane as claimed in claim 1, wherein the reinforcing structure is embedded in the silicone layer.

4. The membrane as claimed in claim 3, wherein the reinforcing structure is embedded in one side of the silicone layer.

5. The membrane as claimed in claim 4, wherein the reinforcing structure is embedded only in one side of the silicone layer.

6. The membrane as claimed in claim 1, wherein a thickness ($D_V$) of the reinforcing structure is, at most, 0.4 mm.

7. The membrane as claimed in claim 6, wherein the thickness of the reinforcing structure is, at most, 0.35 mm.

8. The membrane as claimed in claim 7, wherein the thickness of the reinforcing structure is, at most, 0.3 mm.

9. The membrane as claimed in claim 1, wherein a thickness ($D_S$) of the silicone layer is from 0.03 mm to 0.5 mm.

10. The membrane as claimed in claim 9, wherein the thickness of the silicone layer is from 0.05 mm to 0.4 mm.

11. The membrane as claimed in claim 9, wherein the thickness of the silicone layer is from 0.1 mm to 0.3 mm.

12. The membrane as claimed in claim 1, wherein a thickness ($D_M$) of the membrane is from 0.35 mm to 0.6 mm.

13. The membrane as claimed in claim 12, wherein the thickness of the membrane is from 0.4 mm to 0.5 mm.

14. The membrane as claimed in claim 12, wherein the thickness of the membrane is about 0.45 mm.

15. The membrane as claimed in claim 1, wherein the silicone layer is free from cavities.

16. The membrane as claimed in claim 1, wherein the reinforcing elements are at least one of reinforcing filaments and reinforcing fibers.

17. An oxygenator for gas exchange in a blood-circulation system comprising
   a housing;
   a first internal chamber for blood arranged in the housing;
   a second internal chamber for gas arranged in the housing; and
   at least one membrane comprising a silicone layer and a reinforcing structure which reinforces the silicone layer, wherein the membrane is impermeable to liquid but permeable to gas, wherein the silicone layer comprises silicone rubber,
wherein the silicone layer is free from cavities,
wherein the reinforcing structure comprises polyether sulfone (PES), wherein the reinforcing structure comprises reinforcing elements and intervening spaces, wherein the totality of the intervening spaces forms an area available for flow through the reinforcing structure, wherein a proportion through said area in the reinforcing structure is at least 90% of a total area of the reinforcing structure, and
    wherein the at least one membrane separates the first internal chamber from the second internal chamber,
    wherein a thickness of the silicone layer is smaller than a thickness of the reinforcing structure.

18. The oxygenator as claimed in claim 17, further comprising an exterior hollow cylinder made of a first membrane of the at least one membrane and an interior hollow cylinder arranged in the exterior hollow cylinder and made of a second membrane of the at least one membrane, wherein the first internal chamber is delimited by an internal side of the exterior hollow cylinder and by an external side of the interior hollow cylinder, wherein the second internal chamber is delimited by the interior hollow cylinder, and wherein a third internal chamber is provided which is delimited by an internal side of the housing and by an external side of the exterior hollow cylinder.

19. The oxygenator as claimed in claim 17, further comprising a first membrane and a second membrane which are respectively arranged spirally with respect to a longitudinal axis of the housing, wherein the first internal chamber is delimited by the first membrane and by the second membrane.

20. The oxygenator as claimed in claim 19, wherein the first membrane and the second membrane are retained on a core.

21. The oxygenator as claimed in claim 20, wherein the first membrane and the second membrane are retained on a core which is arranged concentrically with respect to a longitudinal axis of the housing.

22. The oxygenator as claimed in claim 17, wherein the membrane comprises a meandering structure in a plane perpendicular to a longitudinal axis of the housing,
    wherein the meandering structure comprises a plurality of layers oriented parallel to one another,
    wherein two adjacent layers of the plurality of layers are undivided and interconnected by a U-shaped deflection section, and
    wherein the first internal chamber is delimited by two adjacent layers of the meandering structure of the membrane, and wherein the second internal chamber is arranged adjacent to the first internal chamber.

23. A process for the production of a membrane for an oxygenator for gas exchange in a blood-circulation system, comprising the following steps:
    providing a silicone layer and a reinforcing structure;
    using a silicone dispersion to embed the reinforcing structure in the silicone layer; and
    crosslinking the silicone dispersion to give a homogeneous silicone layer into which the reinforcing structure has been embedded such that the membrane is impermeable to liquid but permeable to gas,
wherein the silicone layer comprises silicone rubber,
wherein the silicone layer is free from cavities,
wherein the reinforcing structure comprises polyether sulfone (PES), wherein the reinforcing structure comprises reinforcing elements and intervening spaces, wherein the totality of the intervening spaces forms an area available for flow through the reinforcing structure,
    wherein a proportion through said area in the reinforcing structure is at least 90% of a total area of the reinforcing structure,
    wherein a thickness of the silicone layer is smaller than a thickness of the reinforcing structure.

\* \* \* \* \*